United States Patent [19]

van Andel

[11] Patent Number: Plant 6,688

[45] Date of Patent: Mar. 21, 1989

[54] CARNATION NAMED STAROTIN

[75] Inventor: Jacob van Andel, Aalsmeer, Netherlands

[73] Assignee: Van Staaveren B.V., Aalsmeer, Netherlands

[21] Appl. No.: 101,855

[22] Filed: Sep. 28, 1987

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new carnation cultivar particularly distinguished by its very large, orange-red blooms which are carried upright on long, strong stems having abundant foliage thereby providing very attractive flowers for the cut flower market. This plant is also distinguished by its continuous blooming habit from Spring through Fall and its very good production of blooms.

1 Drawing Sheet

BACKGROUND OF THE NEW PLANT

This new carnation cultivar originated in greenhouse at Aalsmeer, Holland, in 1985 as a sport of the variety 'Stacor' and was propagated by me and under my direction because of the brilliant color and very large size of its bloom. Propagation of this sport was done by means of cuttings and was carried on by me and under my direction for several successive generations, which demonstrated clearly that the novel characteristics of this plant would hold true from generation to generation and appeared to be firmly fixed.

DESCRIPTION OF THE DRAWING

My new carnation variety is illustrated by the accompanying photographic drawing which shows, in full color, a three-fourths face view of a typical flower illustrating the attractive irregular mass arrangement of the flower petals and its novel overall coloration, the color shown being as nearly true to that specified herein as is reasonably possible to obtain by professional photographic procedures.

DESCRIPTION OF THE NEW PLANT

The following is a detailed description of my new carnation cultivar based upon observations of greenhouse grown plants made at Aalsmeer, Holland, in the Fall of 1986, the color designations being specified according to The R.H.S. Colour Chart published by The Royal Horticultural Society of London, England.

THE PLANT

Origin: Sport.
Parentage: The carnation named 'Stacor'.
Classification:
- *Botanic.*—*Dianthus caryophyllus.*
- *Commercial.*—Hybrid carnation.

Form: Tall, erect bush.
Height: Averaging about 100 to 150 cm., depending upon season.
Main stem or cane length: Depends upon growing conditions and season.
Branching character: Normal.
Growth: Vigorous and upright with good strength.
Foliage:
- *Quantity.*—Abundant.

- *Number of leaves.*—Depending on season.
- *Size of leaf.*—Medium.
- *Shape.*—Oblong and curling downwardly with entire margins.
- *Color.*—Upper side — Blue/Green. Under side — Blue/Green.

Rhizomes: Normal.
- *Color.*—White.

THE BUD

Form: Cylindrical and pointed.
Size: Medium.
- *Diameter.*—About 1.5 cm.
- *Length.*—About 3 cm.

Color of petals: When sepals first divide, 45 B.
Sepals: The sepals are normal for carnations and stand up as the bud opens and the flower forms.
Calyx:
- *Shape.*—Pointed.
- *Size.*—Long.
- *Aspect.*—Smooth.
- *Splitting.*—Splitting very rarely occurs.

Flower stem:
- *Length.*—About 120 cm.
- *Character.*—Strong and erect.
- *Color.*—Grey/Green.

THE FLOWER

Blooming habit: Continuous and profuse from Spring through Fall.
Size of bloom: Very large.
- *Diameter.*—About 9 cm.
- *Depth.*—4 to 4.5 cm.

Borne: Singly.
Shape:
- *When flower opens and as it matures.*—High centered and dome shaped.

Petalage:
- *Number of petals.*—From 50 to 70.
- *Arrangement.*—Irregularly imbricated.
- *Form.*—Fan shaped with strongly ruffled margins and very deeply serrate outer ends.
- *Texture.*—Soft.
- *Aspect.*—Shiny.
- *Color.*—All petals, 44 A to 45 B on all sides.

Fragrance: Weak.
Discoloration after full bloom: None.

Persistence: The flower petals hang on and dry.

Lasting quality: About twenty days on the plant and from ten to fifteen days as a cut flower with vase keeping.

Disease resistance: Resistant to *Fusarium oxysporum* as observed at Aalsmeer, Holland.

THE REPRODUCTIVE ORGANS

Stamens:

*Number.*—Moderate.

*Arrangement.*—Around the ovary.

*Anthers.*—Size: Medium. Color: Cream.

*Filaments.*—Length: Up to about 3 mm. Color: White.

*Pollen.*—There is no pollen.

Pistils:

*Number.*—One.

*Styles.*—Length: Long, about 2 mm. Color: White with some red.

*Stigma.*—Color: White.

Character of ovary: Normal.

This plant most nearly resembles the carnation 'Lontarion' (U.S. Plant Pat. No. 5,435).

I claim:

1. The new and distinctive carnation variety and parts thereof, substantially as herein shown and described, characterized by the uniform overall orange-red coloration of its very large blooms, which are carried on long, strong, upright stems having abundant foliage.

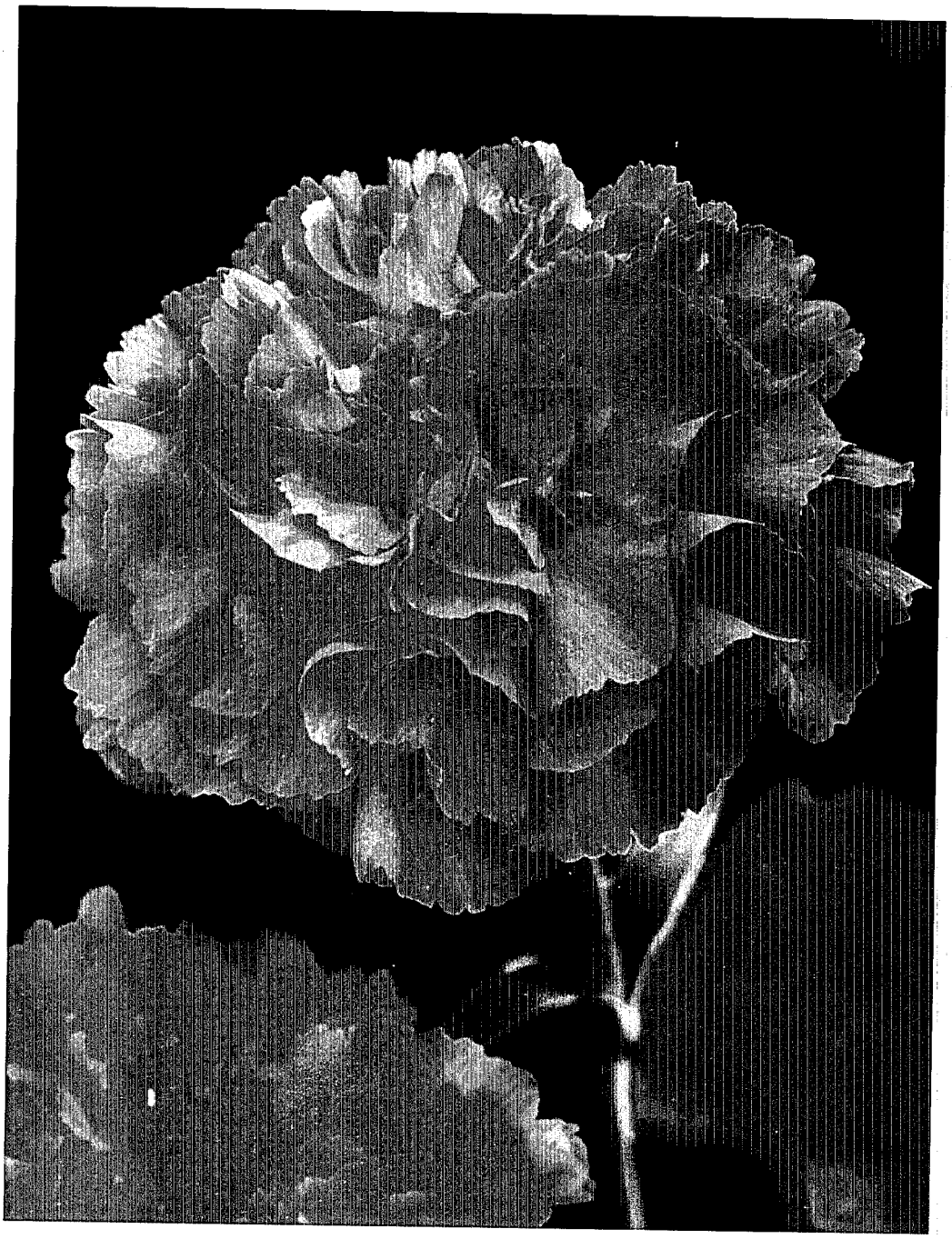

* * * * *